United States Patent [19]
Schouteeten et al.

[11] Patent Number: 5,527,964
[45] Date of Patent: Jun. 18, 1996

[54] ACETALDEHYDE DERIVATIVES, THEIR PREPARATION PROCESS AND THEIR USE

[75] Inventors: Alain Schouteeten, Ezanville; Yani Christidis, Paris, both of France

[73] Assignee: Societe Francaise Hoechst, Puteaux, France

[21] Appl. No.: 431,033

[22] Filed: Apr. 28, 1995

[30] Foreign Application Priority Data

Apr. 29, 1994 [FR] France .................................. 94 05259

[51] Int. Cl.⁶ .................................................. C07C 249/16
[52] U.S. Cl. .......................... 564/249; 549/370; 549/448
[58] Field of Search ............................ 564/249; 549/370, 549/448

[56] References Cited

U.S. PATENT DOCUMENTS

| | | | |
|---|---|---|---|
| 3,959,262 | 5/1976 | Mathais et al. | 564/249 |
| 3,984,451 | 10/1976 | Weiss et al. | 564/249 |

FOREIGN PATENT DOCUMENTS

| | | |
|---|---|---|
| 416499 | 9/1990 | European Pat. Off. |
| 589336 | 9/1993 | European Pat. Off. |
| 602523 | 12/1993 | European Pat. Off. |
| 2233679 | 7/1975 | Germany. |

OTHER PUBLICATIONS

Chemical Abstracts, vol. 110, No. 9, 1989, Columbus, Ohio, US; abstract No. 74995q, & Can. J. Chem., vol. 66, No. 11, 1988, pp. 2839–2848, E. Lai et al.

*Primary Examiner*—Peter O'Sullivan
*Attorney, Agent, or Firm*—Browdy and Neimark

[57] ABSTRACT

Azines of formula (I):

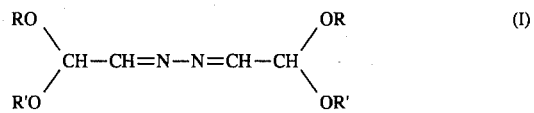

in which R and R' either are identical and represent an alkyl radical containing 1 to 4 carbon atoms or an alkenyl radical containing 3 to 5 carbon atoms, or together form a radical of formula (II):

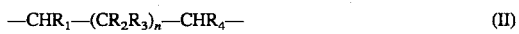

in which $R_1$, $R_2$, $R_3$ and $R_4$, identical or different, represent a hydrogen atom or an alkyl radical containing 1 to 4 carbon atoms and n represents 0 or 1, in their different stereoisomer forms, their preparation process and their use.

6 Claims, No Drawings

ACETALDEHYDE DERIVATIVES, THEIR PREPARATION PROCESS AND THEIR USE

The present invention relates to new acetaldehyde derivatives, their preparation process and their use.

A subject of the present invention is the azines of formula (I):

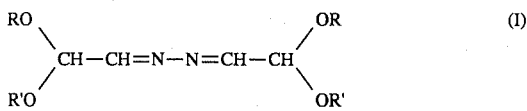

in which R and R' either are identical and represent an alkyl radical containing 1 to 4 carbon atoms or an alkenyl radical containing 3 to 5 carbon atoms, or together form a radical of formula (II):

$$-CHR_1-(CR_2R_3)_n-CHR_4-\quad (II)$$

in which $R_1$, $R_2$, $R_3$ and $R_4$, identical or different, represent a hydrogen atom or an alkyl radical containing 1 to 4 carbon atoms and n represents 0 or 1, in their different stereoisomer forms.

The term "alkyl containing 1 to 4 carbon atoms" can designate, for example, a methyl, ethyl, n-propyl, methylethyl, n-butyl, methyl 1-propyl or methyl 2-propyl radical.

The term "alkenyl containing 3 to 5 carbon atoms" can designate, for example, an allyl, methylallyl, 3,3-dimethyl allyl radical.

The expression "stereoisomer" can designate for example the EE, EZ, ZZ stereoisomers.

A more particular subject of the invention is the products as defined above, characterized in that in formula (I) R and R', being identical, represent an alkyl radical containing 1 to 4 carbon atoms in their different stereoisomer forms.

Among these last-named products, a particular subject of the invention is:

2,2-dimethoxy acetaldehyde-azine, 2,2-diethoxy acetaldehyde-azine, 2,2-dibutoxy acetaldehyde-azine, (5,5-dimethyl 2-oxo 1,3-dioxane)-azine.

According to the invention, the products of formula (I) can be prepared by a process characterized in that hydrazine hydrate is reacted with an acetaldehyde of formula (III):

in which R and R' have the meaning indicated previously, in order to obtain a corresponding product of formula (I).

Under the preferred conditions for implementing the invention, the process described above is carried out:

at ambient temperature, in water, using a stoichiometric quantity of hydrazine hydrate.

The process described above can also be implemented at a higher temperature but generally below 100° C. and using an excess of hydrazine hydrate. It can also be implemented in the presence of a basic catalyst such as an alkaline agent such as, for example, an alkali metal hydroxide, an alkali metal carbonate, an alkali metal hydrogen carbonate. Among these alkaline agents, there can be more preferably mentioned sodium hydroxide, sodium carbonate, potassium carbonate.

The products of formula (III) are either known products or products easily accessible by known processes such as those described in particular in the European Patent Nos. 249,530 and 316,672.

The products of formula (I) above in their different stereoisomer forms have useful chemical properties; in particular they can be converted easily by hydrogenolysis into the corresponding amine of formula (IV):

in which R and R' have the meaning given previously.

These properties justify their use for the preparation of substituted ethylamines of formula (IV) according in particular to one of the processes described in Methoden Der Organischen Chemie—Houben—Weyl—volume XI/1, pages 531–537, Georg Thieme—Stuttgart 1957.

Also a subject of the invention is the use of the azines of formula (I) for obtaining substituted ethylamines of formula (IV). The substituted ethylamines of formula (IV) are extremely useful starting materials for accessing in particular certain usable nitrogenous heterocycles, for example, in the synthesis of products endowed with physiological properties such as certain phthalazines.

The following examples illustrate the present invention without however limiting it.

EXAMPLE 1

340.3 g of an aqueous solution containing 204.2 g (2 moles) of 2,2-dimethoxy ethanal is introduced under agitation, over about 30 minutes and while maintaining the temperature at about 20° C. by external cooling, into 50 g (1 mole) of hydrazine hydrate. Once the introduction is complete, 5.3 g (50 mmoles) of anhydrous sodium carbonate is added to the reaction medium then it is left for 16 hours under agitation at ambient temperature. The expected product crystallizes spontaneously from the reaction medium, it is isolated by filtration, then it is washed by impasting in ice-cooled water and finally it is dried under reduced pressure to a constant weight. In this way 2,2-dimethoxy acetaldehyde-azine is obtained in the form of colourless crystals having a melting point of 56.5°±2° C.

| Microanalysis | | C % | H % | N % | O % |
|---|---|---|---|---|---|
| $C_8H_{16}N_2O_4$ | calculated | 47.04 | 7.90 | 13.72 | 31.34 |
| MW = 204.3 | found | 46.9 | 7.6 | 13.9 | |

Physical analysis—NMR$^1$H (CDCl$_3$) 3.34 ppm, s, 12 H; 4.81 ppm, d, J=4.7 Hz, 2H, 7.53 ppm, d, J=4.7 Hz, 2H. Spectrum in accordance with the proposed structure.

EXAMPLE 2

Example 1 is reproduced placing the sodium carbonate in the hydrazine hydrate before the introduction of the aqueous solution of 2,2-dimethoxy ethanal. In this way pure 2,2-dimethoxy acetaldehyde-azine is obtained with an excellent yield.

EXAMPLE 3

By applying the process described by Ladislas BEREGI, Report, 224, 1508–1509, (1947) for the preparation of the propylamine from propionaldehyde-azine to 2,2-dimethoxy acetaldehyde-azine in solution at 10% by weight in methanol, at 80° C., in the presence of 0.1 gram atom of Raney nickel, under a hydrogen pressure of 10 bars, pure 2,2-dimethoxy ethylamine is obtained in an approximately quantitative yield having a boiling point of 136°±3° C. (literature J. G ERICKSON et al., J. Amer. Chem. Soc., 77, 6640–6641 (1955), B.p.=139.5° C.).

We claim:

1. The azines of formula (I):

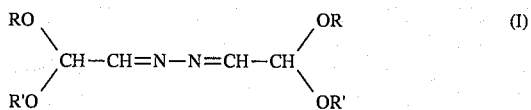

in which R and R' either are identical and represent an alkyl radical containing 1 to 4 carbon atoms or an alkenyl radical containing 3 to 5 carbon atoms, or together form a radical of formula (II):

$$CHR_1-(CR_2R_3)_n-CHR_4- \qquad (II)$$

in which $R_1$, $R_2$, $R_3$ and $R_4$, identical or different, represent a hydrogen atom or an alkyl radical containing 1 to 4 carbon atoms and n represents 0 or 1, in all their different stereoisomer forms.

2. The azines according to claim 1, characterized in that in formula (I), R and R', being identical, represent an alkyl radical containing 1 to 4 carbon atoms in their different stereoisomer forms.

3. 2,2-dimethoxy acetaldehyde-azine.
4. 2,2-diethoxy acetaldehyde-azine.
5. 2,2-dibutoxy acetaldehyde-azine.
6. (5,5-dimethyl 2-oxo dioxane-1,3)-azine.

* * * * *